United States Patent [19]

Freudenreich et al.

[11] Patent Number: 5,334,783
[45] Date of Patent: Aug. 2, 1994

[54] PROCESS FOR THE PREPARATION OF HEXAFLUOROPROPENE

[75] Inventors: Reinhold Freudenreich; Ingolf Mielke; Karl Rettenbeck; Thomas Schöttle, all of Burgkirchen, Fed. Rep. of Germany

[73] Assignee: Hoechst Aktiengesellschaft, Frankfurt am Main, Fed. Rep. of Germany

[21] Appl. No.: 949,348

[22] Filed: Sep. 22, 1992

Related U.S. Application Data

[63] Continuation of Ser. No. 739,732, Jul. 30, 1991, abandoned, which is a continuation of Ser. No. 664,465, Mar. 1, 1991, abandoned, which is a continuation of Ser. No. 488,395, Feb. 27, 1990, abandoned, which is a continuation of Ser. No. 321,966, Mar. 10, 1989, abandoned.

[30] Foreign Application Priority Data

Mar. 14, 1988 [DE] Fed. Rep. of Germany ....... 3808437
Jul. 9, 1988 [DE] Fed. Rep. of Germany ....... 3823370

[51] Int. Cl.$^5$ .............................................. C07C 17/02
[52] U.S. Cl. ...................................... 570/153; 570/155
[58] Field of Search ................................ 570/155, 153

[56] References Cited

U.S. PATENT DOCUMENTS

| | | |
|---|---|---|
| 2,551,573 | 5/1951 | Downing et al. |
| 2,758,138 | 8/1956 | Nelson |
| 2,970,176 | 1/1961 | Ten Eyck et al. |
| 2,979,539 | 4/1961 | Errede et al. |
| 3,397,248 | 8/1968 | Hummel et al. |
| 3,446,858 | 5/1969 | Shingu et al. |
| 3,459,818 | 8/1969 | Ukihashi et al. |
| 3,873,630 | 3/1975 | West |

FOREIGN PATENT DOCUMENTS 1236497 10/1967 Fed. Rep. of Germany.
1062768 3/1967 United Kingdom.

OTHER PUBLICATIONS

V. G. Barabanov et al., *Chem. Abs.* 103:141257w (1985).
A. P. Krasnov et al., *Chem. Abs.* 91:4830x (1979).
*Preparation, Properties, and Technology of Fluorine and Organic Fluoro Compounds*, Ed. C. Slesser et al., McGraw Hill, New York, N.Y. 1951, pp. 592, 593.

*Primary Examiner*—Alan Siegel
*Attorney, Agent, or Firm*—Connolly & Hutz

[57] ABSTRACT

A process for the preparation of hexafluoropropene by thermal cleavage of chlorotetrafluoroethane and/or chlorohexafluoropropane or a mixture of chlorotetrafluoroethane and perfluorocyclobutane at 600° to 1,000° C. and under a pressure of 1 to 1,000 kPa is described. The thermal cleavage is carried out in the presence of at least 0.05 mole of tetrafluoroethylene per mole of chlorotetrafluoroethane and/or chlorohexafluoropropane or mixture of chlorotetrafluoroethane and perfluorocyclobutane employed. By means of this process hexafluoropropene is obtained for a small extra expenditure on apparatus at a good selectivity and in an improved space-time yield.

19 Claims, No Drawings

PROCESS FOR THE PREPARATION OF HEXAFLUOROPROPENE

This application is a continuation of application Ser. No. 07/739,732 filed Jul. 30, 1991 now abandoned which is a continuation of application Ser. No. 07/664,465, filed Mar. 1, 1991 now abandoned which is a continuation of No. 07/488,395 filed Feb. 27, 1990 now abandoned which is a continuation of No. 07/321,966 filed Mar. 10, 1989 now abandoned.

The invention relates to a process for the preparation of hexafluoropropene in accordance with claim 1.

Hexafluoropropene is finding increasing use as a comonomer for the industrial preparation of polymers based on tetrafluoroethylene. It is therefore required to develop low-cost methods of preparing hexafluoropropene. It is known to prepare hexafluoropropene by subjecting substantially fluorinated hydrocarbons to heat treatment at temperatures from 600° to 1,200° C.

The heat treatment of tetrafluoroethylene is described by Miller in "Preparation, Properties and Technology of Fluorine and Organic Fluoro Compounds", McGraw-Hill, New York, 1951, pages 592 and 593. At 655° C. and under normal pressure, hexafluoropropene is obtained in a yield of 42%, whereas at 750° C. the yield of hexafluoropropene falls off considerably and octofluoro-butene is formed to a predominant extent.

The preparation of hexafluoropropene by subjecting tetrafluoroethylene to heat treatment at 750° to 900° C. and under a pressure of 25 to 200 mm Hg (3.3 to 26.7 kPa), 20 to 5,000 g/h of tetrafluoroethylene being fed in per dm³ capacity of the reaction zone is known from U.S. Pat. No. 2,758,138. Instead of pure tetrafluoroethylene it is also possible to use a mixture of tetrafluoroethylene and hexafluoroethane, the latter being recycled into the reaction zone together with unreacted and newly added tetrafluoroethylene.

U.S. Pat. No. 2,970,176 describes a similar process in which the reaction is carried out in the pressure range from 0.2 to 65 psi (1.38 to 448.2 kPa). Instead of pure tetrafluoroethylene, a mixture containing at least 0.05 mole of higher-boiling fluorinated hydrocarbons of the formula

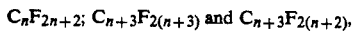

$C_nF_{2n+2}$; $C_{n+3}F_{2(n+3)}$ and $C_{n+3}F_{2(n+2)}$, in which n is 1 to 10 per mole of tetrafluoroethylene is used. The said fluorinated hydrocarbons can be by-products from the pyrolysis of tetrafluoroethylene. They are recycled to the heat treatment while the tetrafluoroethylene consumed is being replaced.

In U.S. Pat. No. 3,446,858 hexafluoropropene is prepared by pyrolysis of tetrafluoroethylene and/or octafluorocyclobutane in the presence of 50 to 95 mole % of steam under adiabatic conditions at 700° to 900° C., the pyrolysis temperature being adjusted by previously mixing the reactants with superheated steam. This process affords good yields of hexafluoropropene, but requires the separation by distillation, which is expensive in terms of apparatus and energy, of the mixture of chlorotetrafluoroethane and octafluorocyclobutane produced in the pyrolysis of chlorodifluoromethane in order to obtain tetrafluoroethylene, and also the admixture, expensive in terms of apparatus, of superheated steam, which, although possible, is not necessary in the new process described later in the text.

In U.S. Pat. No. 3,873,630 hexafluoropropene is prepared by pyrolysis of a mixture of tetrafluoroethylene and carbon dioxide at 790° to 850° C. and under a pressure of 0.75 to 2 atmospheres (73.6 to 196.2 kPa), it being necessary for the partial pressure of the tetrafluoroethylene to be at least 360 mm Hg (48.0 kPa).

Krasnov, Il'ina and Polunina, Nauchn. Tr.-Permsk. Politekh. Inst., 185 (1976), pages 11 to 14 (CA Volume 91, No. 4830x), describe the pyrolysis of chlorotetrafluoroethane at 700° to 850° C., in which the main products formed are 1,1-difluoroethylene and hexafluoropropene.

Barabanov, Volkov, V'yunov and Maksimov, Zh. Obshch. Khim. 55 (4) (1985), pages 868 to 871 (CA Volume 103, No. 41257w), describe the pyrolysis of 1-chloro-1,1,2,2,3,3-hexafluoropropane at 740° to 800° C., in which tetrafluoroethylene, hexafluoropropene and chlorotrifluoroethylene are formed.

The preparation of hexafluoropropene by thermal cleavage of 2-chloro-1,1,1,3,3,3-hexafluoropropane at 650° to 850° C. and dwell times of 3 to 120 seconds is known from U.S. Pat. No. 3,397,248. The maximum yield is 45%.

The preparation of hexafluoropropene by joint pyrolysis of chlorodifluoromethane and 2-chloro-1,1,1,2-tetrafluoroethane in a ratio of 1:1 to 10:1 at 500° to 1,000° C. is also known from British Patent 1,062,768. According to the examples, hexafluoropropene is obtained in selectivities of 42.0 to 79.0%. If, however, 1-chloro-1,1,2,2-tetrafluoroethane, which is produced as the predominant by-product in the industrial pyrolysis of chlorodifluoromethane to give tetrafluoroethylene, is used instead of 2-chloro-1,1,1,2-tetrafluoroethane, difficulties are encountered and poor selectivities in the formation of hexafluoropropene are found, as shown in the comparison test below.

A process has now been found which makes it possible to convert, into hexafluoropropene, at a good selectivity of conversion and at a substantially improved space-time yield, chlorotetrafluoroethane or chlorohexafluoropropane or their mixtures, in particular the compounds 1-chloro-1,1,2,2-tetrafluoroethane and 1-chloro-1,1,2,2,3,3-hexafluoropropane which are the principal byproducts produced in the industrial preparation of tetrafluoroethylene by thermal cleavage of chlorodifluoromethane, or of mixtures of chlorotetrafluoroethane and perfluorocyclobutane, in particular the azeotropic mixture of chlorotetrafluoroethane and perfluorocyclobutane obtained as a byproduct in the industrial preparation of tetrafluoroethylene by thermal cleavage of chlorodifluoromethane.

The new process for the preparation of hexafluoropropene by thermal cleavage of a member of the group consisting of chlorotetrafluoroethane and chlorohexafluoropropane and mixtures thereof or mixtures of chlorotetrafluoroethane with perfluorocyclobutane at a temperature of 600° to 1,000° C. and under a pressure of 1 to 1,000 kPa comprises carrying out the thermal cleavage in the presence of at least 0.05 mole of tetrafluoroethylene per mole of chlorotetrafluoroethane or chlorohexafluoropropane or per mole of the mixture thereof or per mole of a mixture of chlorotetrafluorethane and perfluorocyclobutane.

All the isomers of chlorotetrafluoroethane or of chlorohexafluoropropane are suitable for the new process. Good results are obtained, for example, with 2-chloro-1,1,1,2-tetrafluoroethane. The compounds 1-chloro-1,1,2,2-tetrafluoroethane and 1-chloro-1,1,2,2,3,3-hexafluoropropane are used particularly preferably because they are readily available and have a good action. It is also possible to employ mixtures containing either the two isomers of chlorotetrafluoroethane or isomers of chlorohexafluoropropane or isomers or chlorotetrafluoroethane and chlorohexafluoropropane. Preferred mixtures are those in which the content of one of more compounds in which hydrogen and chlorine are attached to the same carbon is not more than 20% by weight, relative to the total amount of chlorotetrafluoroethane and/or chlorohexafluoropropane employed. Mixtures of this type are obtained as byproducts, for example, in the thermal decomposition of chlorodifluoromethane. It is customary to remove these byproducts by fractional distillation of the main product, tetrafluoroethylene. The thermal cleavage of such distillates at temperatures of 600° to 1,000° C. gives only comparatively poor space-time yields in relation to the formation of hexafluoropropene. Hence the capacity of the reactor in which the thermal cleavage of chlorotetrafluoroethane and/or chlorohexafluoropropane is carried out can only be used to an inadequate extent.

Mixtures of chlorotetrafluoroethane and perfluorocyclobutane are also suitable for the new process. The molar ratio of chlorotetrafluoroethane and perfluorocyclobutane is advantageously 1:10 to 10:1, especially 1:3 to 3:1. Azeotropic mixtures of chlorotetrafluoroethane and perfluorocyclobutane are used particularly preferably because they are readily available and have a good action.

Mixtures of this type are obtained as byproducts, for example, in the thermal decomposition of chlorodifluoromethane. It is customary to remove these byproducts by fractional distillation of the main product tetrafluoroethylene. The thermal cleavage of the said azeotropic mixtures without tetrafluoroethylene at temperatures of 600° to 1,000° C. gives only comparatively poor space-time yields in relation to the formation of hexafluoropropene. Hence the capacity of the reactor in which the thermal cleavage of the mixture of chlorotetrafluoroethane and perfluorocyclobutane is carried out can only be used to an inadequate extent.

It is possible to employ mixtures containing the two isomers of chlorotetrafluoroethane. Preferred mixtures in this case are those in which the content of 2-chloro-1,1,1,2-tetrafluoroethane is not more than 20% by weight, relative to the total amount of chlorotetrafluoroethane employed.

The effect, in accordance with the invention, of the added tetrafluoroethylene starts from 0.05 mole of tetrafluoroethylene per mole of chlorotetrafluoroethane and/or chlorohexafluoropropane or mixture of chlorotetrafluoroethane and perfluorocyclobutane employed. If more than 20 moles of tetrafluoroethylene per mole of chlorotetrafluoroethane and/or chlorohexafluoropropane or mixture of chlorotetrafluoroethane and perfluorocyclobutane is used, difficulties can occur, for example because the cleavage reactor becomes thermally unstable. It is preferable to use 0.5 to 5 moles, especially 1 to 3 moles, of tetrafluoroethylene per mole of chlorotetrafluoroethane and/or chlorohexafluoropropane or mixture of chlorotetrafluoroethane and perfluorocyclobutane employed.

The thermal cleavage according to the invention takes place at temperatures of 600° to 1,000° C., measured on the wall of the reactor at the end of the reaction zone. Below 600° C. an excessively low conversion is generally found. Above 1,000° C. undesirable side reactions take place to an increasing extent, in addition, the thermal cleavage becomes unnecessarily expensive at such high temperatures. It is preferable to carry out the reaction at temperatures of 700° to 900° C., especially at 750° to 860° C.

The pressure of the gas mixture to be employed in accordance to the invention at the reactor inlet should be 1 to 1,000 kPa. Below 1 kPa unfavorable space-time yields are generally achieved; above 1,000 kPa unnecessarily high equipment expenses are generally required, also the selectivity of the formation of hexafluoropropene becomes less favorable and the formation of byproducts increases. It is preferable to carry out the reaction under a pressure of the mixture to be employed in accordance with the invention of 10 to 200 kPa, especially at 20 to 100 kPa.

The average dwell time of the gas mixture in the region of the thermal cleavage is preferably 0.01 to 20 seconds, depending on the cleavage temperature chosen. At fairly high cleavage temperatures, for instance in the range from 850° to 1,000° C., a shorter dwell time will be chosen, for example a dwell time within the range from 0.01 to 1 second, while at low cleavage temperatures, for example within the range from 600° to 700° C., longer dwell times will be chosen, for example within the range from 0.1 to 20 seconds. Good results are obtained at average dwell times from 0.03 to 7 seconds, If a gas mixture composed of tetrafluoroethylene, chlorotetrafluoroethane an d/or chlorohexafluoropropane is employed, average dwell times from 0.08 to 2 seconds are particularly preferred, while if a gas mixture composed of tetrafluoroethylene, chlorotetrafluoroethane and perfluorocyclobutane is employed, average dwell times from 0.05 to 1 second are particularly preferred. At average dwell times higher than 20 seconds the formation of undesirable byproducts is promoted and the formation of a coating also takes place on the reactor surfaces which come into contact with the gas mixture to be thermally cleaved, and this in turn results in a poorer heat transfer. At average dwell times of less than 0.01 second excessively low conversions are generally observed. The average dwell time mentioned above is determined as follows: the volume of the reactor in which the thermal cleavage takes place is divided by the volume of gas occupied by the amount of gas introduced into the reactor in one second at the temperature and pressure conditions prevailing in the reactor.

Before the thermal cleavage, 0.01 to 20 moles, in particular 0.1 to 3 moles, of at least one inert gas can, with advantage, be added per mole of the gas mixture to be employed in accordance with the invention, composed of tetrafluoroethylene, chlorotetrafluoroethane and/or chlorohexafluoropropane, or the gas mixture composed of tetrafluoroethylene, chlorotetrafluoroethane and perfluorocyclobutane. The inert gas can have been heated, before addition, to an elevated temperature, for example 500° to 1,000° C. It is advantageous to use as the inert gas a non-fluorinated substance or a mixture of several non-fluorinated substances which is gaseous under the conditions of the thermal cleavage and does not undergo chemical reaction. Examples of suitable substances are nitrogen, argon, carbon dioxide and particularly water. When inert gases are added to the gas mixture according to the invention, the pressure data quoted above in the text relate to the partial pressure of the gas mixture to be employed in accordance with the invention.

The reactor in which the thermal cleavage takes place can have various shapes. It can, for example, be a simple tube, heated externally, or a reactor, as described in French Patent No. 1,354,341, in which the gaseous fluorinated compounds to be subjected to thermal cleavage are brought to the temperature at which the thermal cleavage takes place essentially by means of the heated inert gas which added. Examples of suitable wall materials, which come into contact with the gases during the thermal cleavage, are nickel, steels of high nickel content, graphite and, in particular, platinum or similar noble metals.

After the thermal cleavage the gas mixture is cooled rapidly, preferably by spraying in water, washed again with water, then treated with aqueous alkali, for example sodium hydroxide solution, and then dried, for example by means of concentrated sulfuric acid, and fractionally distilled. The main reaction product obtained is hexafluoropropene, which has been formed with a good selectivity. The unreacted fractions of tetrafluoroethylene and also, if appropriate, chlorotetrafluoroethane, chlorohexafluoropropane or perfluorocyclobutane are recycled to the process. Undesirable byproducts are removed as waste by known methods.

As already mentioned, the process according to the invention makes it possible to convert, into hexafluoropropene, at a good selectivity and at a substantially improved space-time yield without increasing the cleavage temperature, chlorotetrafluoroethane and/or chlorohexafluoropropane, especially the compounds 1-chloro-1,1,2,2-tetra-fluoroethane and 1-chloro-1,1,2,2,3,3-hexafluoropropane which are the principal byproducts obtained in the preparation of tetrafluoroethylene. The new process also makes it possible to convert, into hexafluoropropene, at a good selectivity and at a substantially improved space-time yield without increasing the cleavage temperature, chlorotetrafluoroethane and perfluorocyclobutane, especially the azeotropic mixtures of chlorotetrafluoroethane which are obtained as a byproduct in the industrial preparation of tetrafluoroethylene. Compared with the known thermal cleavage of chlorotetrafluoroethane or perfluorocyclobutane without added tetrafluoroethylene, the new process requires only a slight extra expenditure on equipment.

The following examples are intended to illustrate the invention in greater detail:

COMPARISON TESTS A TO E AND EXAMPLES 1 TO 6

The substances intended for thermal cleavage, chlorotetrafluoroethane, chlorohexafluoropropane, mixtures of chlorotetrafluoroethane and perfluorocyclobutane and also chlorodifluoromethane, are in each case taken in liquid form from a steel cylinder, vapourized in each case in a vapourizer heated with low-pressure steam and passed into a heated mixing chamber in each case via a heated rotameter. The exact amounts of the substances are determined by weighing the steel cylinders. Tetrafluoroethylene is fed into the mixing chamber in gaseous form via a flow meter. Samples are taken from the mixing chamber and are analyzed by gas chromatography. Steam produced in a further vapourizer is fed into the mixing chamber via a line equipped with parallel heating. The steam rate can be adjusted accurately by means of a pulsation-free metering pump (Type MDP-600 made by Labomatic/Sinsheim).

From the mixing chamber the gas mixture containing steam passes into the reactor, which comprises a U-shaped platinum tube of internal diameter 4 mm and wall thickness 0.25 mm. The platinum tube is mounted in a tubular furnace (type ROK/F-4/140 made by Heraeus/Hanau) which has a controllable heat output of 3.75 kW maximum and heats the platinum tube over a length of 2 m. The internal volume of the heated part of the tube is 25.13 cm$^3$. The internal pressure is measured at the beginning of the platinum tube, while the temperature is measured shortly before the end of the heated part of the tube.

After passing through the reactor the gas mixture subjected to thermal cleavage is passed into a quench column (Diabon DN 50 mm, H=1.05 m made by Sigri/Meitingen) and is chilled there with aqueous hydrochloric acid, at 20° C., containing 15% by weight of HCl. A centrifugal pump delivers this hydrochloric acid at a controllable rate of not more than 100 dm$^3$/h through a heat exchanger, which removes the heat content of the cleaved gas mixture, into a separator, in which the gas mixture and the liquid are separated. The HCl content of this liquid is kept constant by removing part of the hydrochloric acid from the system and replacing by water the volume of liquid removed, and the hydrochloric acid, which again contains 15% by weight of HCl, is recycled to the quench column. After leaving the separator, the mixture of cleaved gas is washed with water, then passed through sulfuric acid in order to dry it and then fed to a gas container, from which samples are taken for analysis by gas chromatography.

The analyses by gas chromatography are carried out on a Hewlett Packard 5890 A with WLD, to which a Shimadzu Integrator C-R3A is connected. The gas chromatograph is equipped with a steel column (10 m, ⅛ inch), packed with Porasil C (80 to 100 mesh, made by Amchro, Sulzbach/Taunus, West Germany). The following temperature program is applied:

Initial temperature: 30° C., 7 min. isotherm
Heating up rate: 1 degr./min.
Final temperature: 100° C.

The carrier gas used is helium (20 ml/min.) and the proportioning volume is 50 to 100 ul. The area percentages measured are converted into weight percentages and the gas rates employed and also obtained after thermal cracking are determined from these in g/h.

For clarity the test results are set out in the table below. In this table the abbreviations have the following meanings:

F124 = mixture of 86% by weight of 1-chloro-1,1,2,2-tetrafluoroethane and 14% by weight of 2-chloro-1,1,1,2-tetrafluoroethane F226 = 1-chloro-1,1,2,2,3,3-hexafluoropropane C$_4$F$_8$—c = Perfluorocyclobutane TFE = Tetrafluoroethylene F22 = Chlorodifluoromethane Residue I = Fluorinated, linear, cyclic, saturated and unsaturated hydrocarbons, in some cases containing chlorine and hydrogen and essentially boiling above hexafluoropropene Residue II = As residue I, but, in addition, hydrogen chloride and small amounts of hydrogen fluoride as well as other fluorinated, linear, cyclic, saturated and unsaturated hydrocarbons, in some cases containing chlorine and hydrogen, formed as byproducts in the course of the reaction.

TABLE

| Example Comparison Test | Gas employed (g/h) | | | | | | | | mole TFE/ mole F124 + $C_4F_8$-c | mole TFE/ mole F124 + F226 | mole $H_2O$/ mole TFE + F124 + $C_4F_8$-c | mole $H_2O$/ mole TFE + F124 + F226 |
|---|---|---|---|---|---|---|---|---|---|---|---|---|
| | F124 | $C_4F_8$-c | F226 | TFE | F22 | $H_2O$ | Residue I | Total | | | | |
| A | 439,0 | — | 1,5 | 0 | 0,3 | 47 | 29,2 | 517 | — | 0 | — | 0,81 |
| 1 | 428,7 | — | 1,6 | 416,4 | 0 | 47 | 38,3 | 932 | — | 1,32 | — | 0,36 |
| B[7] | 249,5 | — | 0,4 | 0 | 266,2 | 27 | 20,9 | 564 | 0 | 0 | 0,82 | 0,82 |
| C | 0 | — | 355,4 | 0 | 0 | 60 | 264,6 | 680 | — | 0 | — | 1,75 |
| 2 | 0 | — | 371,6 | 491,9 | 0,5 | 60 | 246,0 | 1170 | — | 2,47 | — | 0,48 |
| D | 237,3 | — | 152,1 | 0 | 0,2 | 55 | 160,4 | 605 | — | 0 | — | 1,19 |
| 3 | 221,7 | — | 156,1 | 538,8 | 0,8 | 55 | 172,6 | 1145 | — | 2,19 | — | 0,39 |
| 4 | 147,7 | — | 91,2 | 352,4 | 0 | 109 | 78,7 | 779 | — | 2,24 | — | 1,19 |
| E | 128,4 | 331,7 | — | 0 | — | 58 | 119,9 | 638 | 0 | — | 1,24 | — |
| 5 | 92,5 | 222,5 | — | 368,2 | — | 41 | 91,8 | 816 | 2,06 | — | 0,42 | — |
| 6 | 136,2 | 333,4 | — | 788,6 | — | 58 | 141,8 | 1458 | 2,96 | — | 0,31 | — |

| Example Comparison Test | Reactor temperature °C.[1] | Reactor pressure kPa[2] | Partial pressure kPa[3] | Average dwell time s[4] | Gas produced (g/h) | | | | | | Selectivity of conversion to HFP %[6] | Space-time yield of HFP[5] |
|---|---|---|---|---|---|---|---|---|---|---|---|---|
| | | | | | HFP | F124 | $C_4F_8$-c | F226 | TFE | F22 | Residue II + $H_2O$ | |
| A | 850 | 109,7 | 59,0 | 0,18 | 66,8 | 114,2 | — | 2,6 | 112,2 | 21,6 | 199,6 | 27,8 | 2,64 |
| 1 | 860 | 112,5 | 81,1 | 0,10 | 169,6 | 152,0 | — | 3,2 | 284,8 | 22,5 | 299,9 | 50,5 | 6,72 |
| B[7] | 850 | 110,4 | 31,1 | 0,16 | 90,8 | 51,6 | 10,1 | 4,1 | 122,2 | 37,2 | 258,1 | 32,7 | 3,61 |
| C | 840 | 110,5 | 32,3 | 0,16 | 64,0 | 0 | — | 111,0 | 95,3 | 11,9 | 397,8 | 31,7 | 2,48 |
| 2 | 860 | 116,1 | 69,9 | 0,09 | 315,7 | 0 | — | 74,8 | 203,4 | 11,6 | 564,5 | 59,9 | 12,56 |
| D | 850 | 109,0 | 43,6 | 0,17 | 66,7 | 61,4 | — | 44,1 | 110,4 | 18,7 | 303,7 | 30,8 | 2,65 |
| 3 | 850 | 115,9 | 77,0 | 0,09 | 277,0 | 69,9 | — | 45,1 | 305,4 | 20,4 | 427,2 | 63,6 | 10,98 |
| 4 | 860 | 113,1 | 49,8 | 0,09 | 173,7 | 45,3 | — | 27,4 | 154,2 | 9,7 | 368,7 | 53,3 | 7,21 |
| E | 840 | 109,4 | 44,3 | 0,17 | 99,8 | 56,6 | 54,2 | — | 180,3 | 8,5 | 238,6 | 29,9 | 3,93 |
| 5 | 850 | 112,6 | 74,8 | 0,13 | 241,3 | 43,8 | 50,0 | — | 258,0 | 5,5 | 217,4 | 75,6 | 9,58 |
| 6 | 850 | 118,4 | 85,8 | 0,07 | 251,4 | 100,3 | 207,5 | — | 636,3 | 4,4 | 258,1 | 82,3 | 9,97 |

[1] measured at the reactor outlet
[2] measured at the reactor outlet
[3] partial pressure of the gas mixture composed of F124 + F226 + TFE
[4] Relative to the volume of the number of moles employed at the reactor temperature and under a pressure of 100 kPa
[5] in g of HFP per cm$^3$ of reaction space and hour
[6] calculated on the basis of the carbon atom balance
[7] as specified in German Patent 1,236,497

We claim:

1. A process for the preparation of hexafluoropropene by thermal cleavage of a mixture consisting of chlorotetrafluoroethane and perfluorocyclobutane and between 0.5 and 20 mole of tetrafluoroethylene per mole of combined chlorotetrafluoroethane and perfluorocyclobutane at a temperature of from 600° C. to 1,000° C. under a pressure of from 1 kPa to 1,000 kPa.

2. The process as claimed in claim 1, wherein the thermal cleavage is carried out at a temperature of 700° to 900° C.

3. The process as claimed in claim 1, wherein the chlorotetrafluoroethane contains not more than 20% by weight, relative to the total amount thereof, of 2-chloro-1,1,1,2-tetrafluoroethane.

4. The process as claimed in claim 1, wherein the thermal cleavage is carried out in the presence of 0.5 mole to 5 moles of tetrafluoroethylene per mole of said mixture.

5. The process as claimed in claim 1, wherein the dwell time of the mixture and combined tetrafluoroethylene is between 0.02 seconds and 20 seconds.

6. The process of claim 1 wherein the molar ratio of chlorotetrafluoroethane to perfluorocyclobutane in the mixture is from 1:10 to 10:1.

7. The process of claim 6, wherein the molar ratio of chlorotetrafluoroethane to perfluorocyclobutane in the mixture is from 1:3 to 3:1.

8. The process of claim 1, wherein the temperature is between 750° C. and 860° C.

9. A process for the preparation of hexafluoropropene by thermal cleavage of a reaction mixture consisting of:

a) a mixture of chlorotetrafluoroethane and perfluorocyclobutane in a molar ratio of 1:10 to 10:1;

b) 0.5 to 20 moles, based on moles of a), of tetrafluoroethylene; and c) 0.01 to 20 moles, based on combined moles of a) and b), of an inert gas which does not undergo chemical reaction, comprising reacting the mixture at a temperature of 700°–900° C. under a pressure of from 1 kPa to 1,000 kPa.

10. The process of claim 9, wherein the temperature is 750°–860° C.

11. The process of claim 9, wherein the chlorotetrafluoroethane contains not more than 20% by weight, relative to the total amount thereof, of 2-chloro-1,1,1,2-tetrafluoroethane.

12. The process of claim 9, wherein 0.5 to 5 moles of tetrafluoroethylene are present as component b) in the mixture.

13. The process of claim 9, wherein the dwell time of the mixture is 0.02 to 20 seconds.

14. The process of claim 9, wherein the ratio of chlorotetrafluoroethane to perfluorocyclobutane in component a) is 1:3 to 3:1.

15. The process of claim 9, wherein the mixture contains 0.1 to 3 moles of inert gas c).

16. The process of claim 9, wherein the inert gas is selected from the group consisting of nitrogen, carbon dioxide, argon and water.

17. The process of claim 9, wherein the reaction mixture contains 0.01 to 3 moles of inert gas c).

18. The process of claim 9, wherein the reaction mixture contains 0.01 to 0.42 moles of inert gas c).

19. A process for the preparation of hexafluoropropene by thermal cleavage of a mixture consisting essentially of chlorotetrafluoroethane, perfluorocyclobutane, and 0.5 to 20 moles of tetrafluoroethylene per mole of combined chlorotetrafluoroethane and perfluorocyclobutane, at a temperature of from 600° C. to 1,000° C. under a pressure of 1 kPa to 1,000 kPa.

* * * * *

UNITED STATES PATENT AND TRADEMARK OFFICE
CERTIFICATE OF CORRECTION

PATENT NO. : 5,334,783

DATED : 8/2/94

INVENTOR(S) : Freudenriech et al

It is certified that error appears in the above-indentified patent and that said Letters Patent is hereby corrected as shown below:

On the title page, item [75] Inventors: delete the following named inventors:

--Reinhold Freudenreich
 Ingolf Mielke
 Karl Rettenbeck--

Signed and Sealed this

Twenty-second Day of November, 1994

Attest:

BRUCE LEHMAN

Attesting Officer

Commissioner of Patents and Trademarks